(12) United States Patent
Wu et al.

(10) Patent No.: US 11,566,235 B2
(45) Date of Patent: Jan. 31, 2023

(54) MUTANT OF CYCLODEXTRIN GLYCOSYLTRANSFERASE

(71) Applicant: Jiangnan University, Wuxi (CN)

(72) Inventors: Jing Wu, Wuxi (CN); Lingqia Su, Wuxi (CN); Li Du, Wuxi (CN)

(73) Assignee: Jiangnan University, Wuxi (CN)

( * ) Notice: Subject to any disclaimer, the term of this patent is extended or adjusted under 35 U.S.C. 154(b) by 958 days.

(21) Appl. No.: 16/388,688

(22) Filed: Apr. 18, 2019

(65) Prior Publication Data

US 2020/0181585 A1 Jun. 11, 2020

(30) Foreign Application Priority Data

Dec. 7, 2018 (CN) .......................... 201811494800.8

(51) Int. Cl.
| | |
|---|---|
| *C12N 9/10* | (2006.01) |
| *C12N 15/70* | (2006.01) |
| *C12N 15/75* | (2006.01) |
| *A23L 23/00* | (2016.01) |
| *A23L 33/13* | (2016.01) |
| *A23L 29/00* | (2016.01) |

(52) U.S. Cl.
CPC ............ *C12N 9/1048* (2013.01); *A23L 29/06* (2016.08); *A23L 33/13* (2016.08); *C12N 15/70* (2013.01); *C12N 15/75* (2013.01); *C12Y 204/01019* (2013.01); *A23V 2002/00* (2013.01); *C12N 2800/101* (2013.01)

(58) Field of Classification Search
None
See application file for complete search history.

(56) References Cited

U.S. PATENT DOCUMENTS

| | | | | |
|---|---|---|---|---|
| 6,004,790 A | * | 12/1999 | Dijkhuizen | ............ C12P 19/18 435/320.1 |
| 2007/0148287 A1 | * | 6/2007 | Svendsen | ............ C12N 9/2417 435/325 |

* cited by examiner

*Primary Examiner* — Renee Claytor
*Assistant Examiner* — Sharon M. Papciak
(74) *Attorney, Agent, or Firm* — IPro, PLLC; Na Xu

(57) ABSTRACT

The present invention discloses a mutant of cyclodextrin glycosyltransferase and belongs to the fields of gene engineering and enzyme engineering. According to the present invention, a mutant having higher disproportionation activity of cyclodextrin glycosyltransferase is obtained by mutating the cyclodextrin glycosyltransferase. The disproportionation activity of enzymes of mutants V6D, S90G, T168A, T171A, T383A, G608A, and V6D/S90G/T168A/T171A/T383A/G608A, is respectively 1.89 times, 1.21 times, 1.21 times, 1.22 times, 1.32 times, 2.03 times, and 3.16 times that of the wild type enzyme in shake flask fermentations.

10 Claims, No Drawings

Specification includes a Sequence Listing.

MUTANT OF CYCLODEXTRIN GLYCOSYLTRANSFERASE

TECHNICAL FIELD

The disclosure herein relates to a mutant of cyclodextrin glycosyltransferase and belongs to the fields of gene engineering and enzyme engineering.

INCORPORATION OF SEQUENCE LISTING

This application is being filed electronically via EFS-Web and contains a sequence listing entitled "seq.txt" created on Apr. 18, 2019, and is 11,572 bytes in size in Computer Readable Form (CRF). The paper copy of the sequence listing and the CRF are identical and are incorporated herein by reference.

BACKGROUND

Cyclodextrin glycosyltransferase, referred to as CGTase, EC 2.4.1.19, is a major member of the α-amylase family (GH13). It acts as a multifunctional enzyme that catalyzes four different reactions, including three transfructosylation reactions, i.e. a disproportionation reaction, a cyclization reaction and a coupled reaction, and a hydrolysis reaction. Among them, the disproportionation reaction is dominant, and the reaction is to transfer the cut portion of linear oligosaccharide to another receptor, which is an extramolecular transfructosylation reaction. The cyclization reaction is an intramolecular transfructosylation reaction, which is a characteristic reaction of CGTase, and the principle is to transfer the glycoside on the O4 or C4 of the non-reducing end of the linear malto-oligosaccharide to the C1 or O1 of the same linear reducing end. The reverse reaction of the cyclization reaction is a coupled reaction which opens the ring of the cyclodextrin and transfers the glycoside to a linear malt oligomer. CGTase has the activity of catalyzing both the cyclization reaction and the coupled reaction, which is the reason why the product gradually changes from α-cyclodextrin to β-cyclodextrin along the extended time in the process of catalyzing the reaction of starch. When CGTase catalyzes the hydrolysis reaction of starch, the amylose molecules are cut off, and the molecules cut at the two ends are transferred to water molecules to complete the hydrolysis reaction; the activity of the CGTase in catalyzing hydrolysis reaction is relatively low.

CGTase has wide application, the most common of which is the conversion of starch to cyclodextrin by the cyclization reaction. According to the difference of types of cyclodextrin produced, CGTase can be classified into α-CGTase, β-CGTase and γ-CGTase. In addition, it has been reported that CGTase can catalyze starch to produce cyclodextrin with 8 glucose units or more. Through disproportionation and coupled reactions, CGTase can provide monosaccharides or oligosaccharides derived from converted starch or cyclodextrin as donors to various receptor molecules to improve their properties. For example, small molecule sugar is transferred to sucrose or fructose by disproportionation and coupled reactions of the CGTase to produce coupling sugar with an anti-carious function; glycosylation modification of stevioside, rutin, rhamnose and other substances significantly improves their properties, making it more widely used in food, medicine, chemical industry and other fields.

CGTase derived from Bacillus circulans 251 is typical β-CGTase, and its excellent transfructosylation properties can be applied in many fields. However, the disproportionation activity (about 40 U/mL) of the CGTase is lower than that of CGTase derived from other sources, and it is imperative to improve the disproportionation activity of the enzyme.

SUMMARY

One technical problem to be solved by the present invention is to provide a mutant of cyclodextrin glycosyltransferase. The mutant is obtained by mutating one or more amino acid sites in the cyclodextrin glycosyltransferase with the amino acid sequence shown in SEQ ID NO. 2; these sites include: valine (Val) at site 6, serine (Ser) at site 90, threonine (Thr) at site 168, threonine (Thr) at site 171, threonine at site 383 (Thr), and glycine (Gly) at site 608. The activity of the mutant in catalyzing disproportionation reaction is improved.

In one example of the present invention, the amino acid sequence of the cyclodextrin glycosyltransferase derived from B. circulans is shown in SEQ ID NO. 2. The nucleotide sequence of a gene encoding the cyclodextrin glycosyltransferase derived from B. circulans is shown in SEQ ID NO. 1.

In one example of the present invention, the mutant is obtained by mutating the valine (V) at site 6 to aspartic acid in the cyclodextrin glycosyltransferase with the amino acid sequence shown in SEQ ID NO. 2, and naming as V6D.

In one example of the present invention, the mutant is obtained by mutating the serine (S) at site 90 to glycine in the cyclodextrin glycosyltransferase with the amino acid sequence shown in SEQ ID NO. 2, and naming as S90G.

In one example of the present invention, the mutant is obtained by mutating the threonine (T) at site 168 to alanine in the cyclodextrin glycosyltransferase with the amino acid sequence shown in SEQ ID NO. 2, and naming as T168A.

In one example of the present invention, the mutant is obtained by mutating the threonine (T) at site 171 to alanine in the cyclodextrin glycosyltransferase with the amino acid sequence shown in SEQ ID NO. 2, and naming as T171A.

In one example of the present invention, the mutant is obtained by mutating the threonine (T) at site 383 to alanine in the cyclodextrin glycosyltransferase with the amino acid sequence shown in SEQ ID NO. 2, and naming as T383A.

In one example of the present invention, the mutant is obtained by mutating the glycine (G) at site 608 to alanine in the cyclodextrin glycosyltransferase with the amino acid sequence shown in SEQ ID NO. 2, and naming as G608A.

In one example of the present invention, the mutant is obtained by mutating the valine (V) at site 6 to aspartic acid, mutating the serine (S) at site 90 to glycine, mutating the threonine (T) at site 168 to alanine, mutating the threonine (T) at site 171 to alanine, mutating the threonine (T) at site 383 to alanine, and mutating the glycine (G) at site 608 to alanine in the cyclodextrin glycosyltransferase with the amino acid sequence shown in SEQ ID NO. 2, and naming as V6D/S90G/T168A/T171A/T383A/G608A.

Another technical problem to be solved by the present invention is to provide a preparation method of the mutant of cyclodextrin glycosyltransferase, comprising:

(1) determining a mutation site based on the amino acid sequence of cyclodextrin glycosyltransferase derived from Bacillus circulans 251; designing a site-directed mutagenesis mutant primer, and using a vector carrying a cyclodextrin glycosyltransferase gene as a template for site-directed mutagenesis; constructing a plasmid vector containing the mutant;

(2) transforming the mutant plasmid into a host cell;
(3) selecting positive clones for fermentation culture, and purifying the cyclodextrin glycosyltransferase mutants.

In one example of the present invention, the plasmid vector is any one of pUC series, pET series, or pGEX.

In one example of the present invention, the host cell is a bacterial and fungal cell, which is also within the protection scope of the present invention.

In one example of the present invention, the host cell is *Bacillus subtilis, Escherichia coli* or *Bacillus pumilus*.

In one example of the present invention, the bacterium is a Gram-negative or Gram-positive bacterium.

Beneficial Effects of the Present Invention

The present invention obtains a mutant of cyclodextrin glycosyltransferase, and the disproportionation activity of enzyme of mutants V6D, S90G, T168A, T171A, T383A, G608A and V6D/S90G/T168A/T171A/T383A/G608A is respectively 1.89 times, 1.21 times, 1.21 times, 1.22 times, 1.32 times, 2.03 times and 3.16 times that of the wild enzyme in shake flask fermentations. The present invention has certain significance for the industrial production of cyclodextrin glycosyltransferase, and improves the application potential of the enzyme in food, medicine and chemical industries.

DETAILED DESCRIPTION

The examples of the present invention are merely illustrative of the present invention and are not intended to limit the content or scope of the present invention.

The media and detection methods involved in the following examples are as follows:

LB medium (g·L$^{-1}$): Tryptone 10, yeast extract 5, sodium chloride 10.

TB medium (g·L$^{-1}$): Tryptone 12, yeast extract 24, glycerol 5, $KH_2PO_4$ 2.31, $K_2HPO_4·3H_2O$ 16.43, glycine 7.5.

Method for determining the activity of cyclodextrin glycosyltransferase in catalyzing disproportionation reaction: A 50 mmol/L phosphate buffer solution with a 5.5 pH value is taken as a solvent, 12 mM EPS (4,6-ethylidene-p-nitrophenyl-α-D-maltoheptaoside) and a 20 mM maltose solution are respectively prepared, 300 μL of the 12 mM EPS and 300 μL of the 20 mM maltose solution are mixed and preheated in a 50° C. water bath, and 100 μL of a diluted enzyme solution is added; after 10 min of precise reaction, immediate boiling is performed for 10 min to terminate the reaction; after cooling, 100 μL of α-glucosidase and 100 μL of deionized water are added, mixing is performed well and reacting is performed in a water bath at 60° C. for 60 min or more, 100 μL of 1M $Na_2CO_3$ solution is added, mixing is performed well, and finally the absorbance is determined at 400 nm. The activity of the cyclodextrin glycosyltransferase in catalyzing disproportionation reaction is defined as the amount of enzyme that converts one micromole of EPS per minute. (See van der Veen B A, Leemhuis H, Kralj S, et al. Hydrophobic amino acid residues in the acceptor binding site are main determinants for reaction mechanism and specificity of cyclodextrin-glycosyltransferase[J]. Journal of Biological Chemistry, 2001, 276(48): 44557-44562 for the method for determining disproportionation activity.)

Example 1: Expression of Wild Type Cyclodextrin Glycosyltransferase

Glycerol tubes preserved in an earlier stage of a laboratory are inoculated with Cgt/pET20b(+)/BL21(DE3) (Yang Yulu, Wang Lei, Chen Sheng, et al. Optimization of process conditions for the production of β-cyclodextrin by recombinant β-cyclodextrin glycosyltransferase [J]. Biotechnology Bulletin, 2014, 8: 175-181.); and is cultured in an LB liquid medium (containing 100 mg/L ampicillin) for 8 h, and the seed solution is inoculated into a TB liquid fermentation medium (containing 100 mg/L ampicillin) according to an inoculum size of 5%. *Escherichia coli* by shake cultivation at 25° C. is fermented for 48 h, and a certain volume of fermentation broth is centrifuged at 4° C., 12000 rpm for 15 min, and the fermentation supernatant is taken as the crude enzyme solution of wild enzyme.

Example 2: Preparation and Expression of Cyclodextrin Glycosyltransferase Single Mutant (1) Single Mutation Preparation of Cyclodextrin Glycosyltransferase According to the gene sequence of *Bacillus circulans* cyclodextrin glycosyltransferase, primers for introducing single mutations are respectively designed and synthesized, site-directed mutagenesis on the cyclodextrin glycosyltransferase gene Cgt is performed, and whether the encoding genes of the cyclodextrin glycosyltransferase mutants are correct is respectively confirmed by sequencing; the vector carrying the mutant gene is introduced into *Escherichia coli* for expression to obtain single mutant cyclodextrin glycosyltransferase.

PCR amplification of site-directed mutant encoding genes: By the rapid PCR technique, the expression vector Cgt/pET-20b(+) carrying the gene encoding the wild-type cyclodextrin glycosyltransferase is used as a template.

Site-directed mutagenesis primers introducing V6D mutation are:

Forward primer with nucleotide sequence shown in SEQ ID NO. 3:

```
5'-CCGGATACCAGCGATAGCAACAAGCAG-3'
(the underlined is a mutated base)
```

Reverse primer with nucleotide sequence shown in SEQ ID NO. 4:

```
5'-CTGCTTGTTGCTATCGCTGGTATCCGG-3'
(the underlined is a mutated base)
```

Site-directed mutagenesis primers introducing S90G mutation are:

Forward primer with nucleotide sequence shown in SEQ ID NO. 5:

```
5'-CTATAGCATTATCAACTACGGCGGTGTGAATAATACGG-3'
(the underlined is a mutated base)
```

Reverse primer with nucleotide sequence shown in SEQ ID NO. 6:

```
5'-CCGTATTATTCACACCGCCGTAGTTGATAATGCTATAG-3'
(the underlined is a mutated base)
```

Site-directed mutagenesis primers introducing T168A mutation are:
Forward primer with nucleotide sequence shown in SEQ ID NO. 7:

```
5'-CTGGGCGGTTATGCCAATGACACCC-3'
(the underlined is a mutated base)
```

Reverse primer with nucleotide sequence shown in SEQ ID NO. 8:

```
5'-CTGGGCGGTTATGCCAATGACACCC-3'
(the underlined is a mutated base)
```

Site-directed mutagenesis primers introducing T171A mutation are:
Forward primer with nucleotide sequence shown in SEQ ID NO. 9:

```
5'-CGGTTATACCAATGACGCCCAAAATCTGTTTC-3'
(the underlined is a mutated base)
```

Reverse primer with nucleotide sequence shown in SEQ ID NO. 10:

```
5'-GAAACAGATTTTGGGCGTCATTGGTATAACCG-3'
(the underlined is a mutated base)
```

Site-directed mutagenesis primers introducing T383A mutation are:
Forward primer with nucleotide sequence shown in SEQ ID NO. 11:

```
5'-CCAAGTTTTAGCGCGAGCACGACGG-3'
(the underlined is a mutated base)
```

Reverse primer with nucleotide sequence shown in SEQ ID NO. 12:

```
5'-CCGTCGTGCTCGCGCTAAAACTTGG-3'
(the underlined is a mutated base)
```

Site-directed mutagenesis primers introducing G608A mutation are:
Forward primer with nucleotide sequence shown in SEQ ID NO. 13:

```
5'-CAAAATGTGTATCTGACGGCCAGCGTGAGCGAACTGGG-3'
(the underlined is a mutated base)
```

Reverse primer with nucleotide sequence shown in SEQ ID NO. 14:

```
5'-CCCAGTTCGCTCACGCTGGCCGTCAGATACACATTTTG-3'
(the underlined is a mutated base)
```

PCR reaction systems: 0.5 µL of 20 µM forward primers and 0.5 µL of 20 µM reverse primers, 4 µL of dNTPs Mix, 10 µL of 5*PS Buffer, 0.5 µL of 2.5 U/µL PrimeStar polymerase, 0.5 µL of template, and the balance of double distilled water filled 50 µL.

PCR conditions: Pre-denaturation at 94° C. for 4 min; followed by 25 cycles (94° C. for 10 s, 55° C. for 5 s, 72° C. for 7 min 50 s), extension at 72° C. for 10 min; finally, heat preservation at 4° C. The PCR product is detected by 1% agarose gel electrophoresis.

The above verified correct PCR product is digested with Dpn I and transferred into *Escherichia coli* JM 109 competent cells; an LB agar plate containing 100 mg/L ampicillin is coated with the transformed product; after culturing at 37° C. for overnight, two single colonies are picked from the agar plate and an LB liquid medium is inoculated with the two single colonies; after 8 h, extracting the plasmid and sequencing it to confirm that the result is correct. The correctly sequenced plasmid is transferred into *Escherichia coli* BL21 (DE3) to obtain recombinant *Escherichia coli* expressing a single mutant.

(2) Expression of Mutants

The LB liquid medium (containing 100 mg/L ampicillin) is respectively inoculated with the recombinant *Escherichia coli* expressing the single mutant prepared in step (1) of the present example, and culturing is performed for 8 h, and a TB liquid fermentation medium (containing 100 mg/L ampicillin) are inoculated with the seeds according to an inoculum size of 5%. The *Escherichia coli* by shake cultivation at 25° C. is fermented for 48 h, a certain volume of fermentation broth is centrifuged at 4° C., 12000 rpm for 15 min, and the fermentation supernatant is taken as the crude enzyme solution of the single mutant.

Example 3: Preparation and Expression of Cyclodextrin Glycosyltransferase Six-Mutant (1) Six-Mutation Preparation of Cyclodextrin Glycosyltransferase A plasmid carrying the gene encoding the mutant V6D constructed in Example 2 is used as a template for the six-mutation, and according to the primers for S90G, T168A, T383A and G608A site-directed mutagenesis designed in Example 2, site-directed mutagenesis is performed on the plasmid carrying the gene encoding the mutant V6D by the rapid PCR technique to obtain a cyclodextrin glycosyltransferase V6D/S90G/T168A/T383A/G608A five-mutant. Then, a new primer is designed by using the plasmid of the V6D/S90G/T168A/T383A/G608A five-mutant as a template, and T171A mutation is introduced to construct a cyclodextrin glycosyltransferase V6D/S90G/T168A/T171A/T383A/G608A six-mutant.

The site-directed mutagenesis primers introducing T171A mutation are changed to:
Forward primer with nucleotide sequence shown in SEQ ID NO. 15:

```
5'-CGGTTATGCCAATGACGCCCAAAATCTGTTTC-3'
(the underlined is a mutated base)
```

Reverse primer with nucleotide sequence shown in SEQ ID NO. 16:

```
5'-GAAACAGATTTTGGGCGTCATTGGCATAACCG-3'
(the underlined is a mutated base)
```

(2) Expression of Mutants

An LB liquid medium (containing 100 mg/L ampicillin) is inoculated with the recombinant *Escherichia coli* expressing the mutant prepared in step (1) of the present example, and culturing is performed for 8 h; a TB liquid fermentation medium (containing 100 mg/L ampicillin) is inoculated with the seeds according to an inoculum size of 5%. The *Escherichia coli* by shake cultivation at 25° C. is fermented for 48 h, a certain volume of fermentation broth is centrifuged at 4° C., 12000 rpm for 15 min, and the fermentation supernatant is taken as the crude enzyme solution of the six-mutant.

Example 4: Analysis of Disproportionation Activity of Cyclodextrin Glycosyltransferase The disproportionation activity of fermentation supernatants obtained in Example 1, Example 2 and Example 3 is respectively determined. The $OD_{600\ nm}$ and the enzyme disproportionation activity of wild-type cyclodextrin glycosyltransferase (WT) and mutants subjected to shake flask cultivation for 48 h are shown in Table 1. The results show that the enzyme disproportionation activity of all mutants is higher than that of the wild type. The disproportionation activity of enzyme of mutants V6D, S90G, T168A, T171A, T383A, G608A and V6D/S90G/T168A/T171A/T383A/G608A is respectively 1.89 times, 1.21 times, 1.21 times, 1.22 times, 1.32 times, 2.03 times and 3.16 times of the wild enzyme in shake flask fermentations.

TABLE 1

$OD_{600\ nm}$ and enzyme disproportionation activity of wild and mutant enzymes of cyclodextrin glycosyltransferase in shake flask fermentation

| Enzyme | $OD_{600\ nm}$ | Enzyme activity (U/mL) |
|---|---|---|
| WT | 11.2 | 44.1 |
| V6D | 7.1 | 83.3 |
| S90G | 8.8 | 53.4 |
| T168A | 10.1 | 53.4 |
| T171A | 10.3 | 53.8 |
| T383A | 9.9 | 58.2 |
| G608A | 8.9 | 89.7 |
| V6D/S90G/T168A/T171A/T383A/G608A | 6.9 | 139.2 |

What is claimed is:

1. A mutant of cyclodextrin glycosyltransferase, consisting of one of the following mutations:
   (a) a mutation of the valine (V) at site 6 to aspartic acid (V6D) in the cyclodextrin glycosyltransferase with the amino acid sequence set forth in SEQ ID NO: 2;
   (b) a mutation of the threonine (T) at site 171 to alanine (T171A) in the cyclodextrin glycosyltransferase with the amino acid sequence set forth in SEQ ID NO: 2;
   (c) a mutation of the threonine (T) at site 383 to alanine (T383A) in the cyclodextrin glycosyltransferase with the amino acid sequence set forth in SEQ ID NO: 2;
   (d) a mutation of the glycine (G) at site 608 to alanine (G608A) in the cyclodextrin glycosyltransferase with the amino acid sequence set forth in SEQ ID NO: 2; or
   (e) a mutation of the valine (V) at site 6 to the aspartic acid, a mutation of the serine (S) at site 90 to glycine, a mutation of the threonine (T) at site 168 to alanine, a mutation of the threonine (T) at site 171 to alanine, a mutation of the threonine (T) at site 383 to alanine, and a mutation of the glycine (G) at site 608 to alanine,
   wherein the cyclodextrin glycosyltransferase is derived from *Bacillus circulans*, and
   wherein the amino acid sequence of the cyclodextrin glycosyltransferase derived from *Bacillus circulans* is set forth in SEQ ID NO: 2.

2. The mutant cyclodextrin glycosyltransferase of claim 1, wherein the mutation is a mutation of the valine (V) at site 6 to aspartic acid (V6D) in the cyclodextrin glycosyltransferase with the amino acid sequence set forth in SEQ ID NO: 2.

3. The mutant cyclodextrin glycosyltransferase of claim 1, wherein the mutation is a mutation of the threonine (T) at site 171 to alanine (T171A) in the cyclodextrin glycosyltransferase with the amino acid sequence set forth in SEQ ID NO: 2.

4. The mutant cyclodextrin glycosyltransferase of claim 1, wherein the mutation is a mutation of the threonine (T) at site 383 to alanine (T383A) in the cyclodextrin glycosyltransferase with the amino acid sequence set forth in SEQ ID NO: 2.

5. The mutant cyclodextrin glycosyltransferase of claim 1, wherein the mutation is a mutation of the glycine (G) at site 608 to alanine (G608A) in the cyclodextrin glycosyltransferase with the amino acid sequence set forth in SEQ ID NO: 2.

6. The mutant cyclodextrin glycosyltransferase of claim 1, wherein the mutation is a mutation of the valine (V) at site 6 to the aspartic acid, a mutation of the serine (S) at site 90 to glycine, a mutation of the threonine (T) at site 168 to alanine, a mutation of the threonine (T) at site 171 to alanine, a mutation of the threonine (T) at site 383 to alanine, and a mutation of the glycine (G) at site 608 to alanine.

7. A method for constructing the cyclodextrin glycosyltransferase mutant of claim 1, comprising:
   (1) designing a site-directed mutagenesis mutant primer according to the determined mutation site, and performing site-directed mutagenesis using a vector carrying a cyclodextrin glycosyltransferase gene as a template; constructing a plasmid vector comprising a gene encoding the mutant;
   (2) transforming the mutant plasmid vector into a host cell;
   (3) selecting positive clones for fermentation culture, and centrifuging the supernatant to obtain a crude enzyme solution of the cyclodextrin glycosyltransferase mutant.

8. The method of claim 7, wherein the plasmid vector is any one of pUC series, pET series, or pGEX.

9. The method of claim 7, wherein the plasmid vector is cgt/pET20b(+).

10. The method of claim 7, wherein the host cell is a bacterial or fungal cell.

* * * * *

SEQUENCE LISTING

<160> NUMBER OF SEQ ID NOS: 16

<210> SEQ ID NO 1
<211> LENGTH: 2061
<212> TYPE: DNA
<213> ORGANISM: Artificial sequence
<220> FEATURE:
<223> OTHER INFORMATION: Synthetic DNA

<400> SEQUENCE: 1

```
gcaccggata ccagcgttag caacaagcag aatttcagca cggatgtgat ctatcagatc    60
ttcacggacc gcttcagcga tggtaacccg gcgaacaacc caacgggcgc agcattcgat   120
ggcacctgca ccaatctgcg tctgtactgt ggtggtgact ggcagggcat catcaacaag   180
atcaacgatg gttacctgac cggtatgggt gttacggcaa tctggatcag ccaaccagtg   240
gaaaatatct atagcattat caactacagc ggtgtgaata atacggcata ccacggctat   300
tgggcccgtg atttcaaaaa aaccaatccg gcgtatggca cgatcgcgga ttttcagaat   360
ctgattgcag cggcacatgc aaaaaacatt aaagtgatta tcgattttgc gccgaatcac   420
accagcccag cgagcagcga tcaaccgagc ttcgcggaaa acggtcgcct gtatgacaat   480
ggtaccctgc tgggcggtta ccaatgac acccaaaatc tgtttcatca aacggtggt   540 accgatttta gcaccaccga gaatggtatt tacaagaacc tgtacgatct ggcggatctg   600
aaccataata atagcacggt tgacgtttat ctgaaagatg cgattaagat gtggctggat   660
ctgggcattg acgcattcg tatggatgcg gttaaacaca tgccattcgg ttggcaaaag   720
agctttatgg ccgcagttaa caattacaag ccggttttca cctttggcga atggttcctg   780
ggcgtgaatg aagtgagccc ggagaaccac aagtttgcga atgagagcgg tatgagcctg   840
ctggacttcc gtttcgcgca gaaagtgcgt caagttttc gtgataacac ggataatatg   900
tatggcctga aggcgatgct ggaaggtagc gccgcagact atgcgcaagt tgacgatcaa   960
gtgaccttca ttgacaatca cgatatggaa cgcttccatg cgagcaacgc gaatcgtcgc  1020
aagctggaac aagcgctggc gtttacccctg acgagccgcg tgttccggc gatctactat  1080 ggtacggaac agtatatgag cggtggcacc gacccggaca atcgtgcgcg tatcccaagt  1140
tttagcacga gcacgacggc ctaccaggtg attcagaaac tggcaccact gcgcaaatgt  1200
aacccagcca ttgcgtacgg tagcacgcaa gaacgttgga ttaacaacga cgttctgatc  1260
tacgaacgta aatttggcag caacgttgcc gttgttgcgg tgaaccgtaa cctgaacgca  1320
```

```
ccggcaagca tcagcggcct ggtgaccagc ctgccacaag gcagctataa cgatgttctg    1380
ggtggtctgc tgaacggtaa cacgctgagc gttggtagcg gcggtgcagc aagcaatttt    1440
acgctggcag ccggcggcac ggcagtttgg caatatacgg ccgcaaccgc gacgccgacc    1500
attggccatg tgggtccaat gatggcgaag ccaggtgtga ccattacgat tgatggtcgc    1560
ggcttcggca gcagcaaagg caccgtttac tttggtacga ccgccgttag cggtgcggat    1620
attacgagct gggaggatac ccaaatcaaa gttaagatcc cagccgttgc gggtggcaac    1680
tataacatca aggttgcgaa cgcggcaggt accgccagca atgtttacga caatttcgag    1740
gttctgagcg gcgaccaagt tagcgtgcgc tttgtggtga acaatgcaac cacggcgctg    1800
ggtcaaaatg tgtatctgac gggcagcgtg agcgaactgg gtaattggga cccggccaaa    1860
gcgatcggcc cgatgtacaa ccaagtggtg tatcagtatc cgaattggta ctatgatgtg    1920
agcgtgccag ccggtaaaac gatcgagttc aagttcctga agaaacaggg cagcaccgtg    1980
acgtgggaag gtggtagcaa tcatacgttt acggccccaa gcagcggtac ggccacgatt    2040
aacgtgaatt ggcaaccgta a                                               2061
```

<210> SEQ ID NO 2
<211> LENGTH: 686
<212> TYPE: PRT
<213> ORGANISM: Artificial Sequence
<220> FEATURE:
<223> OTHER INFORMATION: Protein translated from synthetic DNA

<400> SEQUENCE: 2

```
Ala Pro Asp Thr Ser Val Ser Asn Lys Gln Asn Phe Ser Thr Asp Val
1               5                   10                  15

Ile Tyr Gln Ile Phe Thr Asp Arg Phe Ser Asp Gly Asn Pro Ala Asn
            20                  25                  30

Asn Pro Thr Gly Ala Ala Phe Asp Gly Thr Cys Thr Asn Leu Arg Leu
        35                  40                  45

Tyr Cys Gly Gly Asp Trp Gln Gly Ile Ile Asn Lys Ile Asn Asp Gly
    50                  55                  60

Tyr Leu Thr Gly Met Gly Val Thr Ala Ile Trp Ile Ser Gln Pro Val
65                  70                  75                  80

Glu Asn Ile Tyr Ser Ile Ile Asn Tyr Ser Gly Val Asn Asn Thr Ala
                85                  90                  95

Tyr His Gly Tyr Trp Ala Arg Asp Phe Lys Lys Thr Asn Pro Ala Tyr
            100                 105                 110

Gly Thr Ile Ala Asp Phe Gln Asn Leu Ile Ala Ala His Ala Lys
        115                 120                 125

Asn Ile Lys Val Ile Ile Asp Phe Ala Pro Asn His Thr Ser Pro Ala
    130                 135                 140

Ser Ser Asp Gln Pro Ser Phe Ala Glu Asn Gly Arg Leu Tyr Asp Asn
145                 150                 155                 160

Gly Thr Leu Leu Gly Gly Tyr Thr Asn Asp Thr Gln Asn Leu Phe His
                165                 170                 175

His Asn Gly Gly Thr Asp Phe Ser Thr Thr Glu Asn Gly Ile Tyr Lys
            180                 185                 190

Asn Leu Tyr Asp Leu Ala Asp Leu Asn His Asn Asn Ser Thr Val Asp
        195                 200                 205

Val Tyr Leu Lys Asp Ala Ile Lys Met Trp Leu Asp Leu Gly Ile Asp
    210                 215                 220
```

-continued

Gly Ile Arg Met Asp Ala Val Lys His Met Pro Phe Gly Trp Gln Lys
225                 230                 235                 240

Ser Phe Met Ala Ala Val Asn Asn Tyr Lys Pro Val Phe Thr Phe Gly
            245                 250                 255

Glu Trp Phe Leu Gly Val Asn Glu Val Ser Pro Glu Asn His Lys Phe
                260                 265                 270

Ala Asn Glu Ser Gly Met Ser Leu Leu Asp Phe Arg Phe Ala Gln Lys
            275                 280                 285

Val Arg Gln Val Phe Arg Asp Asn Thr Asp Asn Met Tyr Gly Leu Lys
    290                 295                 300

Ala Met Leu Glu Gly Ser Ala Ala Asp Tyr Ala Gln Val Asp Asp Gln
305                 310                 315                 320

Val Thr Phe Ile Asp Asn His Asp Met Glu Arg Phe His Ala Ser Asn
                325                 330                 335

Ala Asn Arg Arg Lys Leu Glu Gln Ala Leu Ala Phe Thr Leu Thr Ser
            340                 345                 350

Arg Gly Val Pro Ala Ile Tyr Tyr Gly Thr Glu Gln Tyr Met Ser Gly
        355                 360                 365

Gly Thr Asp Pro Asp Asn Arg Ala Arg Ile Pro Ser Phe Ser Thr Ser
370                 375                 380

Thr Thr Ala Tyr Gln Val Ile Gln Lys Leu Ala Pro Leu Arg Lys Cys
385                 390                 395                 400

Asn Pro Ala Ile Ala Tyr Gly Ser Thr Gln Glu Arg Trp Ile Asn Asn
                405                 410                 415

Asp Val Leu Ile Tyr Glu Arg Lys Phe Gly Ser Asn Val Ala Val Val
            420                 425                 430

Ala Val Asn Arg Asn Leu Asn Ala Pro Ala Ser Ile Ser Gly Leu Val
        435                 440                 445

Thr Ser Leu Pro Gln Gly Ser Tyr Asn Asp Val Leu Gly Gly Leu Leu
450                 455                 460

Asn Gly Asn Thr Leu Ser Val Gly Ser Gly Gly Ala Ala Ser Asn Phe
465                 470                 475                 480

Thr Leu Ala Ala Gly Gly Thr Ala Val Trp Gln Tyr Thr Ala Ala Thr
                485                 490                 495

Ala Thr Pro Thr Ile Gly His Val Gly Pro Met Met Ala Lys Pro Gly
            500                 505                 510

Val Thr Ile Thr Ile Asp Gly Arg Gly Phe Gly Ser Ser Lys Gly Thr
        515                 520                 525

Val Tyr Phe Gly Thr Thr Ala Val Ser Gly Ala Asp Ile Thr Ser Trp
530                 535                 540

Glu Asp Thr Gln Ile Lys Val Lys Ile Pro Ala Val Ala Gly Gly Asn
545                 550                 555                 560

Tyr Asn Ile Lys Val Ala Asn Ala Ala Gly Thr Ala Ser Asn Val Tyr
                565                 570                 575

Asp Asn Phe Glu Val Leu Ser Gly Asp Gln Val Ser Val Arg Phe Val
            580                 585                 590

Val Asn Asn Ala Thr Thr Ala Leu Gly Gln Asn Val Tyr Leu Thr Gly
        595                 600                 605

Ser Val Ser Glu Leu Gly Asn Trp Asp Pro Ala Lys Ala Ile Gly Pro
610                 615                 620

Met Tyr Asn Gln Val Val Tyr Gln Tyr Pro Asn Trp Tyr Tyr Asp Val
625                 630                 635                 640

Ser Val Pro Ala Gly Lys Thr Ile Glu Phe Lys Phe Leu Lys Lys Gln

```
                    645                 650                 655
        Gly Ser Thr Val Thr Trp Glu Gly Gly Ser Asn His Thr Phe Thr Ala
                660                 665                 670
        Pro Ser Ser Gly Thr Ala Thr Ile Asn Val Asn Trp Gln Pro
                675                 680                 685

<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
ccggatacca gcgatagcaa caagcag                                           27

<210> SEQ ID NO 4
<211> LENGTH: 27
<212> TYPE: DNA
<213> ORGANISM: Artificial Sequence
<220> FEATURE:
<223> OTHER INFORMATION: Synthetic DNA

<400> SEQUENCE: 4
ctgcttgttg ctatcgctgg tatccgg                                           27

<210> SEQ ID NO 5
<211> LENGTH: 38
<212> TYPE: DNA
<213> ORGANISM: Artificial Sequence
<220> FEATURE:
<223> OTHER INFORMATION: Synthetic DNA

<400> SEQUENCE: 5
ctatagcatt atcaactacg gcggtgtgaa taatacgg                               38

<210> SEQ ID NO 6
<211> LENGTH: 38
<212> TYPE: DNA
<213> ORGANISM: Artificial Sequence
<220> FEATURE:
<223> OTHER INFORMATION: Synthetic DNA

<400> SEQUENCE: 6
ccgtattatt cacaccgccg tagttgataa tgctatag                               38

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA

<400> SEQUENCE: 7
ctgggcggtt atgccaatga caccc                                             25

<210> SEQ ID NO 8
<211> LENGTH: 25
<212> TYPE: DNA
<213> ORGANISM: Artificial Sequence
<220> FEATURE:
<223> OTHER INFORMATION: Synthetic DNA

<400> SEQUENCE: 8
ctgggcggtt atgccaatga caccc                                             25
```

<210> SEQ ID NO 9
<211> LENGTH: 32
<212> TYPE: DNA
<213> ORGANISM: Artificial Sequence
<220> FEATURE:
<223> OTHER INFORMATION: Synthetic DNA

<400> SEQUENCE: 9
cggttatacc aatgacgccc aaaatctgtt tc              32

<210> SEQ ID NO 10
<211> LENGTH: 32
<212> TYPE: DNA
<213> ORGANISM: Artificial Sequence
<220> FEATURE:
<223> OTHER INFORMATION: Synthetic DNA

<400> SEQUENCE: 10
gaaacagatt ttgggcgtca ttggtataac cg              32

<210> SEQ ID NO 11
<211> LENGTH: 25
<212> TYPE: DNA
<213> ORGANISM: Artificial Sequence
<220> FEATURE:
<223> OTHER INFORMATION: Synthetic DNA

<400> SEQUENCE: 11
ccaagtttta gcgcgagcac gacgg                      25

<210> SEQ ID NO 12
<211> LENGTH: 25
<212> TYPE: DNA
<213> ORGANISM: Artificial Sequence
<220> FEATURE:
<223> OTHER INFORMATION: Synthetic DNA

<400> SEQUENCE: 12
ccgtcgtgct cgcgctaaaa cttgg                      25

<210> SEQ ID NO 13
<211> LENGTH: 28
<212> TYPE: DNA
<213> ORGANISM: Artificial Sequence
<220> FEATURE:
<223> OTHER INFORMATION: Synthetic DNA

<400> SEQUENCE: 13
gttcaagttc ctggagaaac agggcagc                   28

<210> SEQ ID NO 14
<211> LENGTH: 28
<212> TYPE: DNA
<213> ORGANISM: Artificial Sequence
<220> FEATURE:
<223> OTHER INFORMATION: Synthetic DNA

<400> SEQUENCE: 14
gctgccctgt ttctccagga acttgaac                   28

<210> SEQ ID NO 15
<211> LENGTH: 32
<212> TYPE: DNA
<213> ORGANISM: Artificial Sequence
<220> FEATURE:

```
<223> OTHER INFORMATION: Synthetic DNA

<400> SEQUENCE: 15
cggttatgcc aatgacgccc aaaatctgtt tc                                32

<210> SEQ ID NO 16
<211> LENGTH: 32
<212> TYPE: DNA
<213> ORGANISM: Artificial Sequence
<220> FEATURE:
<223> OTHER INFORMATION: Synthetic DNA

<400> SEQUENCE: 16
gaaacagatt tgggcgtca ttggcataac cg                                 32
```